United States Patent [19]
Min et al.

[11] Patent Number: 5,836,976
[45] Date of Patent: Nov. 17, 1998

[54] CARDIOVERSION ENERGY REDUCTION SYSTEM

[75] Inventors: Xiaoyi Min, Plymouth; Li Wang, White Bear Township; Rahul Mehra, Stillwater; Paul J. DeGroot, Brooklyn Park; Walter H. Olson, North Oaks; Luc R. Mongeon; Michael R. S. Hill, both of Minneapolis, all of Minn.

[73] Assignee: Medtronic, Inc., Minneapolis, Minn.

[21] Appl. No.: 846,747

[22] Filed: Apr. 30, 1997

[51] Int. Cl.$^6$ ........................................ A61N 1/39
[52] U.S. Cl. ................................................ 607/6
[58] Field of Search .................... 607/4, 5, 6, 8, 607/14, 17

[56] References Cited

U.S. PATENT DOCUMENTS

| | | |
|---|---|---|
| 3,952,750 | 4/1976 | Mirowski . |
| 4,577,633 | 3/1986 | Berkovits . |
| 4,587,970 | 5/1986 | Holley . |
| 4,726,380 | 2/1988 | Vollmann . |
| 4,830,006 | 5/1989 | Haluska . |
| 4,880,005 | 11/1989 | Pless . |
| 4,969,464 | 11/1990 | Callaghan . |
| 5,074,301 | 12/1991 | Gill . |
| 5,117,824 | 6/1992 | Keimel . |
| 5,193,536 | 3/1993 | Mehra . |
| 5,207,219 | 5/1993 | Adams . |
| 5,235,976 | 8/1993 | Spinelli ........................ 607/25 |
| 5,269,298 | 12/1993 | Adams et al. . |
| 5,282,836 | 2/1994 | Kreyenhagen . |
| 5,314,448 | 5/1994 | Kroll et al. . |
| 5,334,221 | 8/1994 | Bardy . |
| 5,366,485 | 11/1994 | Kroll et al. . |
| 5,405,364 | 4/1995 | Noren et al. ................ 607/17 |
| 5,431,687 | 7/1995 | Kroll ............................ 607/8 |
| 5,500,005 | 3/1996 | Strandberg et al. ........ 607/17 |
| 5,549,642 | 8/1996 | Min et al. . |

FOREIGN PATENT DOCUMENTS

| | | |
|---|---|---|
| 9218198 | of 0000 | WIPO . |
| 9218198 | 10/1992 | WIPO . |

OTHER PUBLICATIONS

"Automatic Tachycardia Recognition", Arzbaecher, et al. Pace vol. 7, May–Jun., 1984 Part II, pp. 541–546.

Alessie et al, "Regional Control of Atrial Fibrillation by Rapid Pacing in Conscious Dogs", published in *Circulation*, vol.84, No.4, Oct. 1991, pp. 1689–1697.

*Primary Examiner*—Jeffrey R. Jastrzab
*Attorney, Agent, or Firm*—Reed A. Duthler; Harold R. Patton

[57] ABSTRACT

In an implantable pacemaker/cardioverter/defibrillator, a system for correlating the delivery of a cardioversion therapy to an optimum point or phase of the respiratory cycle of the patient to effect delivery of the therapy when the impedance between the cardioversion electrodes is minimized. In a first application for use with cardioversion electrodes located substantially in contact with the heart chamber, the optimum point or phase is at the end of inspiration. In a second application for use with at least one cardioversion electrode located remotely from the heart chamber, the optimum point or phase is at end expiration or beginning of inspiration. The cardioversion therapy is delivered in synchrony with a ventricular sense event, if present. If the optimum point or phase of the respiratory cycle cannot be determined during a therapy time, a pre-shock may be delivered to elicit a respiration cycle through a stimulated contraction of the diaphragm.

24 Claims, 5 Drawing Sheets

CARDIOVERSION ENERGY REDUCTION SYSTEM

CROSS-REFERENCE TO RELATED APPLICATIONS

Reference is hereby made to commonly assigned, co-pending U.S. patent application Ser. Nos. 08/230,578 filed Apr. 21, 1994 now abandoned, for TREATMENT OF ATRIAL FIBRILLATION by Luc R. Mongeon et al.; 08/495,251 filed Jun. 27, 1995, now U.S. Pat. No. 5,713,924 for DEFIBRILLATION THRESHOLD REDUCTION PACING SYSTEM by Xiaoyi Min et al.; Ser. No. 08/230,577 filed Apr. 21, 1994 now U.S. Pat. No. 5,562,708 for METHOD AND APPARATUS FOR TREATMENT OF ATRIAL FIBRILLATION by William J. Combs et al.; Ser. No. 08/640,046 filed Apr. 30, 1996 now U.S. Pat. No. 5,683,429 for ATRIAL FIBRILLATION PREVENTION PACING SYSTEM by Rahul Mehra; and 08/846,938 filed on even date herewith for CARDIOVERSION ENERGY REDUCTION SYSTEM by Luc Mongeon et al., all of which deal with related subject matter.

FIELD OF THE INVENTION

The present invention generally relates to implantable cardioverter-defibrillators and, more specifically to a system for correlating the delivery of a cardioversion therapy to an optimum phase of the respiratory cycle of the patient to effect delivery of the therapy when the impedance between the cardioversion electrodes is minimized.

BACKGROUND OF THE INVENTION

By way of definition, in the field of automatic implantable arrhythmia control devices, the term "cardioversion" or "cardioverter" refers to the process of and device for discharging relatively high energy electrical shocks in excess of 1.0 Joule into or across cardiac tissue to arrest or "cardiovert" a tachyarrhythmia of a cardiac chamber. Delivery of cardioversion shocks may or may not be synchronized with a cardiac depolarization or rhythm and may be applied to arrest a malignant atrial or ventricular tachycardia or fibrillation with a selectable or programmable pulse energy. The termination of high rate tachycardias with lesser energy electrical pulses or bursts has also been referred to as "cardioversion" The arrest of atrial or ventricular fibrillation by higher energy shocks is referred to as "defibrillation", and defibrillation has been characterized in the past as a form of cardioversion. Products have been described and sold as "implantable cardioverter/defibrillator" (ICD) systems for providing synchronized cardioversion shocks or and unsynchronized defibrillation shocks and as "pacemaker/cardioverter/defibrillator" (PCD) systems for providing additional staged therapies of anti-tachyarrhythmia pacing, synchronized cardioversion shocks and unsynchronized defibrillation shocks. In the following description and claims, it is to be assumed that the terms "cardioversion" and "defibrillation" and variants thereof are interchangeable, and that use of one term is inclusive of the other device or operation, unless specific distinctions are drawn between them in the context of the use. For convenience, the term "cardioversion" or "cardioversion/defibrillation" will be used unless a form of defibrillation therapy is specifically referred to.

Tachyarrhythmias are episodes of high rate cardiac depolarizations, typically occurring in one chamber of the heart but which may be propagated from one chamber to the other, and are distinguished from sinus tachycardias that physiologically accompany exercise to provide adequate cardiac output. Tachyarrhythmias that are sufficiently high in rate and chaotic compromise cardiac output from the affected chamber(s), leading to loss of consciousness and death, in the case of ventricular fibrillation, or weakness and dizziness, in the case of atrial fibrillation or flutter and non-sinus atrial and ventricular tachycardias. Atrial fibrillation and flutter are debilitating, due to the loss of atrial cardiac output contribution and interference with ventricular filling, but not immediately life threatening unless it leads to ventricular fibrillation. High rate atrial and ventricular tachycardias may exhibit a more organized rhythm but also may disable the patient and can lead to fibrillation if untreated.

Fibrillation has generally been treated by means of high energy cardioversion/defibrillation shocks, which, in the context of implantable anti-arrhythmia devices, are applied by means of large surface area cardioversion electrodes, including an electrode on or in the chamber to be defibrillated. The battery life of an ICD or PCD device depends on the amount of energy expended in delivering a therapy and the delivery frequency. The high energy level employed in order to defibrillate consumes considerable energy in the range of 1.0–30.0 Joules per delivered shock. The high energy level is employed in order to simultaneously depolarize the bulk of the heart chamber to be defibrillated, which will include tissues in all stages of the depolarization-repolarization cycle at the time the pulse is delivered.

For patients experiencing ventricular fibrillation, the delivered cardioversion/defibrillation shock energy is necessary to save the patient's life and is usually not perceived by the patient because of the loss of consciousness shortly following onset of the arrhythmia. Accuracy of diagnosis and delivery of a cardioversion shock having sufficient energy to cardiovert the rhythm as quickly as possible are paramount concerns because the efficacy of the shock decreases with time lapse from onset of the symptoms.

Patients experiencing high rate atrial tachycardias and atrial fibrillation/flutter typically do not lose consciousness, and the condition is usually not life threatening. The intentional or inadvertent delivery of the cardioversion shock therapy by an ICD or PCD device is startling and painful to a degree that is assumed to be proportional to the shock energy level.

It was recognized early in the development of external ventricular defibrillators that a lower energy synchronous cardioversion shock could be employed to interrupt a high rate ventricular tachycardia, if the shock delivery was synchronized to a ventricular depolarization event, i.e. the R-wave. The lower energy threshold is attributed to the assumption that more of the ventricular muscle mass is intrinsically depolarized at this time, thereby requiring less cardioversion energy to depolarize the remaining ventricular muscle mass. If synchronization to a ventricular depolarization can be achieved, staged therapy ICD and PCD devices deliver somewhat lower energy cardioversion shocks to the affected chamber. Ventricular synchronized atrial cardioversion and defibrillation is employed to ensure that the cardioversion/defibrillation pulse is delivered before the "vulnerable period" associated with the re-polarization of the heart.

Episodes of atrial tachyarrhythmias occur frequently and are debilitating to the patient, if not life threatening. Unfortunately, the quantity of electrical energy required to cardiovert or defibrillate the atria is sufficient, in most cases, to cause a sudden, propagated pain in the patient's chest area or to stun the patient. Typically reported defibrillation thresholds (in humans) of 2–3 Joules are required between transvenous lead bearing electrodes placed to provide atrial cardioversion pathways between the right atrium (RA) and the coronary sinus (CS) or the superior vena cava (SVC) and the CS. Other atrial electrode systems may require up to 4.0–10 Joules (in humans) to reliably cardiovert. Significant discomfort and often intolerable pain is associated with such atrial cardioversion/defibrillation shock therapies in this range, resulting in sedation of some patients and refusal to accept the therapy by other patients. Moreover, there is concern that the attempt to defibrillate the atria will itself induce ventricular fibrillation leading to the death of the patient. In the hospital setting, the patient is carefully monitored, and induced ventricular fibrillation may be defibrillated. However, the clinical procedure still entails enough risk that drug therapies are preferred, and atrial defibrillation is used only after other therapies fail.

The same concerns have delayed the development of implantable atrial defibrillators so that patients prone to bouts of atrial fibrillation or flutter could remain ambulatory. One possible approach that has been widely published is to combine the atrial and ventricular fibrillation detection and cardioversion/defibrillation capabilities in a single implantable system so that induced ventricular fibrillation could be terminated. Such a device is disclosed in U.S. Pat. No. 5,549,642, issued to Min et al. The Incontrol Metrix TM atrial defibrillator, currently in clinical evaluation, does not provide the capability of treating induced ventricular tachyarrhythmias and therefore relies upon shock delivery criteria to avoid induction of ventricular tachyarrhythmias. In the context of atrial cardioversion, a proposed pacemaker/defibrillator is disclosed in PCT Publication No. WO 92/18198 by Adams et al. where the synchronization of the high voltage atrial cardioversion shock is to the R-wave in an effort to avoid inducing ventricular tachycardia or fibrillation. In either case, synchronization to an R-wave in a high rate, irregular EGM has proven to be difficult to accomplish and not always effective to avoid inducing ventricular fibrillation.

Faced with these difficulties, attempts have been made to first make the cardiac rhythm more regular so that the P-wave or R-wave may be detected and to then apply the synchronous cardioversion therapy. In commonly assigned U.S. Pat. No. 5,193,536, a PCD system is described where the high atrial or ventricular rate is made more regular by delivering overdrive pacing pulses to capture the heart and by using the last overdrive pulse delivered as a synchronization event to time the delivery of the cardioversion shock. Another method is disclosed in U.S. Pat. No. 5,074,301 where a single pacing pulse is delivered to the atrium to allow the cardioversion shock to be delivered in the atrial refractory period. It is not suggested that the overdrive pacing pulses affect the cardioversion threshold.

In U.S. Pat. Nos. 5,314,448 and 5,366,485, an ICD is described having a set of cardioversion electrodes arranged around the patient's heart. When fibrillation is detected, the high output capacitors begin to be charged. As they are charged or after full charge is achieved, a "pre-treatment" of the fibrillating heart muscle is commenced through the generation of a train of pulses from the voltage on the output capacitors and delivery of the pulses across the cardioversion electrodes. The capacitors are recharged and at the end of the recharge time period, the high energy cardioversion pulse is delivered across the cardioversion electrodes. It is stated that the pre-treatment pulses begin the process of organizing the chaotically contracting myocardial cells and result in a reduction of cardioversion threshold and the total energy expended. It is emphasized that the pre-treatment pulse voltages are well in excess of pacing level voltages and that the same cardioversion electrodes are employed to deliver the energy to the same myocardial cells as will be defibrillated by the cardioversion pulse. In this manner, the pre-treatment pulses are delivered into the high current density regions of the current pathways in the heart chamber between the spaced apart cardioversion electrodes.

In the above-referenced '251 application, a method and apparatus for terminating fibrillation is disclosed using a burst of pacing energy, high frequency pulses applied into a low current density region of the cardiac tissue in the chamber in fibrillation prior to the delivery of one or more cardioversion energy pulses. The burst of pacing energy pulses is delivered between the pace/sense electrodes located in the low current density region of the cardioversion pathway around and through the heart chamber defined by the cardioversion energy distributed between the spaced apart cardioversion electrodes. The burst of pacing energy pulses injected into the low current density region results in the lowering of the cardioversion threshold, and the decreased energy cardioversion pulse effectively terminates the fibrillation episode. The burst of pacing energy pulses appears to develop a refractory island in the low energy region of the heart chamber that may itself lower the cardioversion energy, and also appears to prevent ectopic beats originating in the low energy region from re-fibrillating the heart.

Recently, the theoretical possibility of employing low energy pacing level pulses (i.e. less than 0.05 joules) to terminate atrial fibrillation has been explored. For example, in the recent article "Regional Control of Atrial Fibrillation by Rapid Pacing in Conscious Dogs", by Allessie et al, published in *Circulation*, Volume 84, No. 4, October 1991, pages 1689–1697, the ability of pacing pulses to capture a small area of fibrillating atrial tissue, if applied during a specified time interval synchronized to the sensed depolarization waveform at the pacing electrode site, is reported. However, the depolarization wavefront created by such pulses does not propagate through the entire chamber due to the varying polarization states of the tissue surrounding the stimulation site. Consequently, it has not been demonstrated that this approach can defibrillate a heart chamber actually in fibrillation.

It is generally believed that the delivery of pacing pulse bursts to the atrium can induce atrial fibrillation, unless the delivery is synchronized to P-waves to assure that the pulse bursts occur within the refractory period of the atrium. This effect is discussed in U.S. Pat. No. 5,334,221 which discloses a device which provides pulse bursts, synchronized to a P-wave, to the SA nodal fat pad in the atrium to reduce the sinus rate of patients who suffer from angina.

Despite this general belief, it has also been proposed to avoid synchronizing the delivered pacing pulse or burst to a detected depolarization to interrupt atrial fibrillation or flutter. In the '577 application, the pacing pulses are simultaneously delivered at multiple sites distributed over a substantial portion of the atria or atrium to be treated. Rather than attempt to synchronize the delivered pulses to the high rate atrial electrogram sensed at a stimulation site, simultaneous pulse delivery at the multiple dispersed sites is intended to eventually result in capture of the atrial tissue at one or more of the stimulation sites. It is theorized that the propagation of the depolarization wavefront created in response to the delivered pacing pulse, toward cardiac tissue closely adjacent the site at which capture initially occurs, increases the probability that the adjacent tissue will be in an appropriate stage of the depolarization-repolarization cycle to be captured by the next pulse in the burst. As pulses of the burst continue to be delivered, therefore, the amount of atrial tissue captured should gradually increase, with the end result of capturing a sufficient amount of atrial tissue to terminate fibrillation.

Similarly, in the '578 application, a series of low energy pulse bursts is delivered, separated by defined inter-burst intervals, and including bursts unsynchronized to atrial heart depolarizations. Detection of termination of atrial fibrillation during inter-burst intervals results in cancellation of further pulse bursts to prevent re-induction of fibrillation.

Despite these advances, a need continues to exist for atrial and ventricular cardioversion systems that can cardiovert high rate atrial and ventricular tachycardias and atrial fibrillation/flutter at lower energy levels to decrease energy consumption and pain perceived by the patient.

SUMMARY OF THE INVENTION

It is therefore an object of the present invention to provide a cardioversion/defibrillation method and apparatus that operates to cardiovert the atria or ventricles with lower energy cardioversion pulses.

The present invention is directed to the termination of a tachyarrhythmia of a patient's heart chamber. In recognition that the heart chamber volume and the autonomic tone for sustenance of fibrillation of the heart chamber, particularly the atria, is influenced by the respiratory cycle, the delivery of the cardioversion therapy is timed to a point or phase of the respiratory cycle when the impedance between the cardioversion electrodes is minimized. The optimum point or phase of the cycle depends in part on the chamber to be cardioverted and the location of the cardioversion electrodes with respect to the chamber.

In a first application of the invention for use with cardioversion electrodes located substantially in contact with the heart chamber, the optimum point or phase is at end inspiration in the respiratory cycle. The pulse may be synchronized to the patient's normal breathing cycle or the patient may maintain the end inspiration state by holding his/her breath. The increase in lung volume during inspiration is associated with a decrease in the volume of the chamber and shortening the current pathways within the chamber. The increase in lung volume also increases the volume impedance around the heart, since the lungs are full of air, and the current pathways of the cardioversion shock are concentrated in the myocardium. Advantageously, for the conscious patient, the perception of pain attendant a cardioversion shock delivery may be lessened because the diaphragm is contracted and not as readily stimulated by the delivered cardioversion/defibrillation pulse at the end of inspiration. In addition, the activity of the vagal nerves applied to the heart is lessened, which reduces the autonomic influences on dispersion of refractoriness.

In the second application of the invention, where at least one of the cardioversion electrodes is more remotely located, e.g. a subcutaneously placed separate patch cardioversion electrode or ICD can cardioversion electrode, then the optimum point or phase is preferably at the end of expiration or beginning of inspiration. In this case, the impedance between the cardioversion electrodes depends on the volume of air and tissue between the electrodes which may be minimized when the lungs are deflated. In any case, the selection of the optimum point or phase may be made by the physician in a patient work-up during or following implantation of the system. If the selected point for delivery of cardioversion/defibrillation therapy is during the initial phase of inspiration, lung volume will still be relatively reduced and the diaphragm will be contracting so that the delivered cardioversion/defibrillation pulse will not trigger an additional, unexpected inspiration and the activity of the vagal nerves applied to the heart will be lessened as discussed above.

In a further aspect of the invention, the presence or absence of the respiratory cycle is determined over a therapy time window during the charging of high voltage output capacitors for delivering a cardioversion shock therapy. If the respiratory cycle does not exhibit the programmed phase or point during the time window, a low energy pre-shock may be delivered to stimulate the diaphragm and intercostal muscles into contracting. The cardioversion therapy may thereafter be delivered synchronized to the desired phase of the induced respiratory cycle. Preferably, a comprehensive system of the invention provides the cardioversion therapy at the optimal time of the respiratory cycle and timed with respect to the cardiac cycle to avoid delivery of the cardioversion therapy in the vulnerable period of the ventricles.

The cardioversion therapy may optionally comprise any of the efficacious combinations of cardioversion/defibrillation shocks, pre-treatments or atrial pacing therapies described above and elsewhere in the continuing development of the field of atrial cardioversion. In the event that synchronization to the optimal point or phase of the respiratory cycle is not possible over a given number of attempts or maximum therapy time period, an unsynchronized back-up therapy may be delivered.

While the invention is believed primarily beneficial in the cardioversion of atrial fibrillation, as a practical matter, it may be difficult to distinguish atrial fibrillation from atrial flutter and high rate atrial tachycardias which may be simultaneously present in some patients. It is believed that the methods and apparatus of the present invention are beneficial in terminating any such atrial tachyarrhythmia.

The present invention also has application to the delivery of ventricular cardioversion therapies to the ventricles to treat ventricular tachyarrhythmias, particularly high rate ventricular tachycardias where the patient is conscious and/or breathing, as described above. However, the delivery of the prescribed therapy cannot be unduly delayed in the attempt to synchronize the delivery to the appropriate point or phase of the respiratory cycle.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

The present invention is particularly directed to the treatment of atrial tachyarrhythmias and to hemodynamically compromising but not necessarily life threatening ventricular tachycardias that are frequently treated by application of a cardioversion therapy delivered in synchrony with a ventricular depolarization. In recognition that the cardiac volume, the inter-electrode impedance and the autonomic tone for sustenance of at least atrial fibrillation/flutter are influenced by the respiratory cycle, an impedance plethysmography method is employed in the present invention to monitor the respiration cycle. In one embodiment, the delivery of the cardioversion therapy is timed to the maximum lung volume at the end of inspiration associated with a reduction in the heart chamber volume and shortening the current pathways between intracardiac or epicardial cardioversion electrodes and an increase in the impedance in the chest and lungs. In another embodiment, the delivery is timed to the minimum lung volume which effectively reduces the inter-electrode impedance between a remote cardioversion electrode and an electrode on or in the heart.

Figure 1:
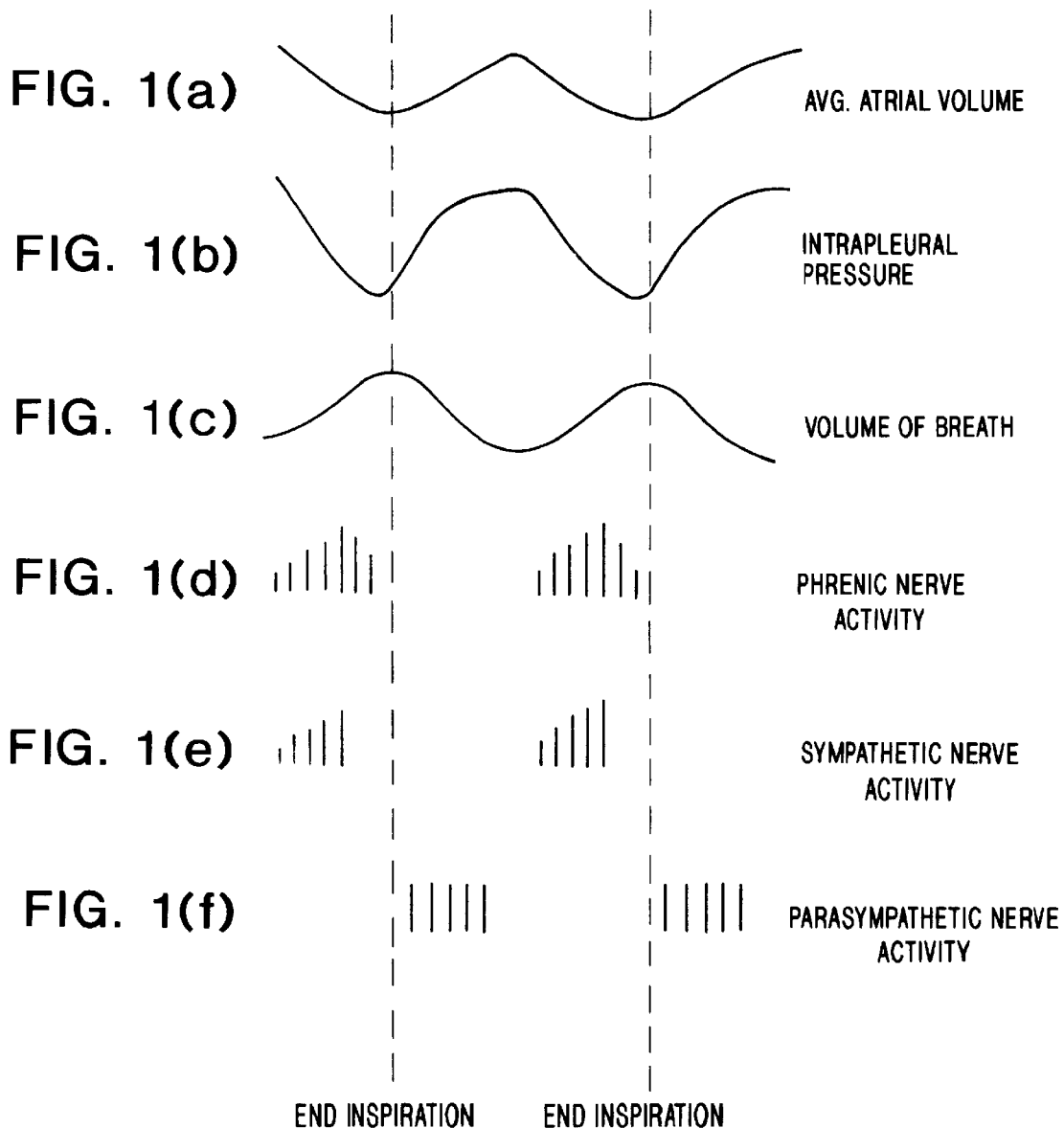
FIG. 1 is a graphical depiction of the respiratory cycle and the pressure waves, volume waves and nerve activity attendant to breathing.

Turning to FIG. 1, it represents the pressure and air volume waveforms of respiratory cycles and their affect on atrial volume as well as attendant nerve signal bursts to the heart that tie intrinsic heart rate and excitability of myocardial cells to the respiratory cycle. In each respiratory cycle, and as shown in tracing (c), the air volume in the lungs increases from the start of inspiration to a maximum at an the end of inspiration and then decreases during expiration to the end of expiration, where it may remain until the start of the next inspiration. The inspiration phase of the respiration cycle is effected by contraction of the diaphragm in response to the phrenic nerve firings shown in tracing (d) which continue until the end of inspiration. The inspiration phase is accompanied by the sympathetic nerve firings that are shown in tracing (e). The expiration phase is accompanied by parasympathetic nerve firings shown in tracing (f). The atria respond to the sympathetic nerve firings by increasing excitability, thereby making them easier to cardiovert or defibrillate. Somewhat conversely, the atria respond to parasympathetic nerve firings by shortening refractory intervals, which can have the effect of decreasing a prevailing AF cycle length, presumably making the atria more difficult to cardiovert or defibrillate.

As shown in tracing (c) of FIG. 1, during inspiration, the volume of air in the lungs increases due to the decrease in the air pressure within the lungs shown in tracing (b). The average atrial volume shown in tracing (a) varies inversely with lung volume and is decreased at the end inspiration point. In one aspect of the present invention, delivery of an atrial cardioversion/defibrillation therapy, particularly between atrial cardioversion electrodes in contact with the heart is timed to the detection of the end inspiration point or the inspiration phase leading up to the end inspiration point. In a second aspect of the present invention, delivery of an atrial cardioversion/defibrillation therapy, particularly between atrial cardioversion electrodes including an electrode in contact with the heart and a remote electrode located subcutaneously in the pectoral of axillary regions is timed from the detection of the end of expiration or during the initial portion of the inspiration phase. The cardiac cycle shown in FIG. 1 varies between 0.5 seconds (120 bpm) at moderate exercise or excitement and 1.0 seconds (60 bpm) at rest, and consequently several cardiac cycles may be completed during the respiratory cycle, so that delivery of a ventricular cardioversion pulse synchronized to a ventricular depolarization or an atrial cardioversion/defibrillation pulse appropriately timed to avoid the vulnerable period of the ventricles should in most cases be possible during the desired phase of the respiratory cycle. Alternatively the patient may prolong the desired point or phase of the respiratory cycle by stopping respiration at the desired point or phase of the respiratory cycle for a few seconds.

Figure 2:
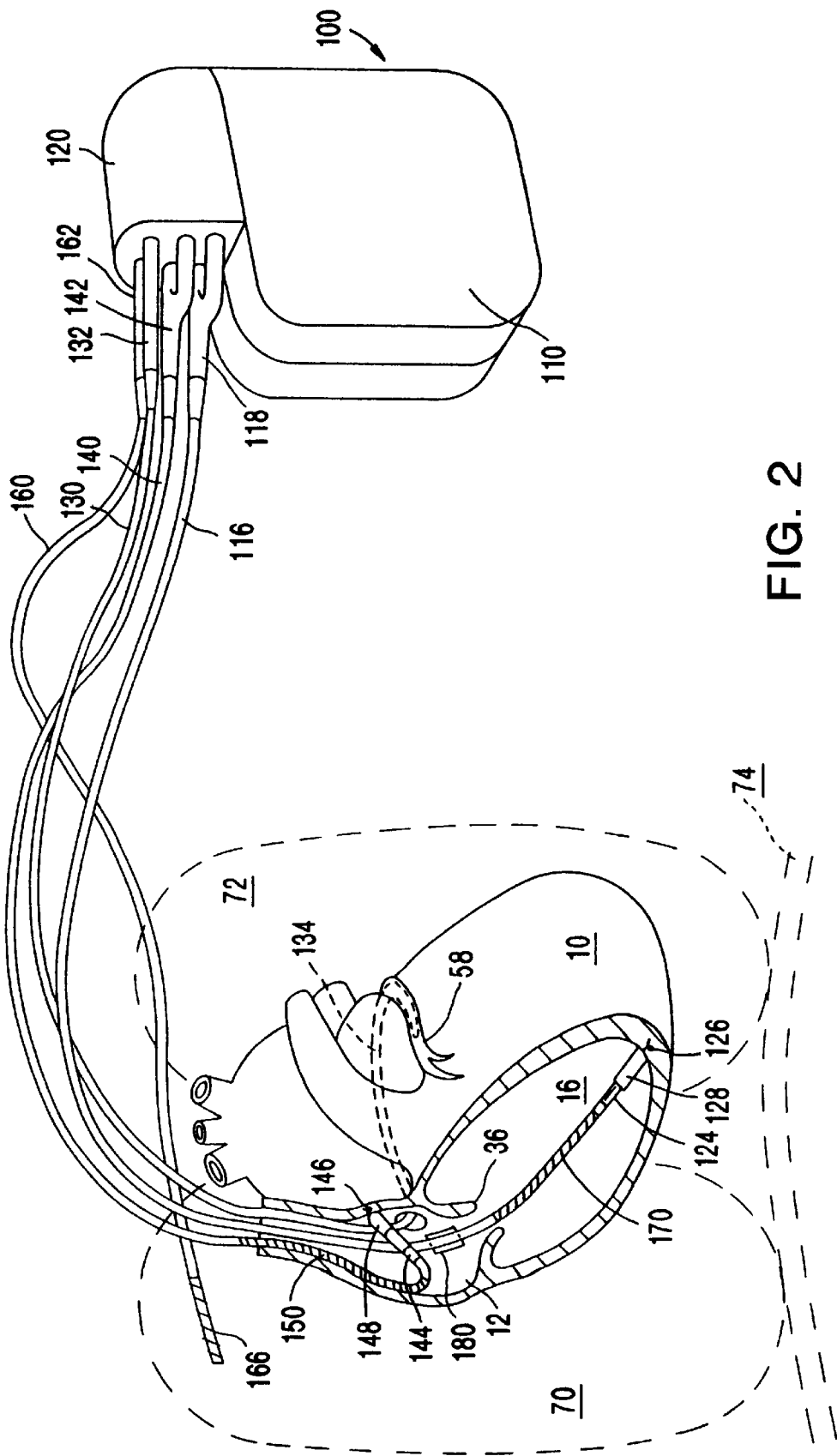
FIG. 2 is a schematic view of an illustrative comprehensive ICD or PCD IPG and lead system in which the embodiments and variations of present invention may be advantageously selectively employed or combined.
Figure 3:
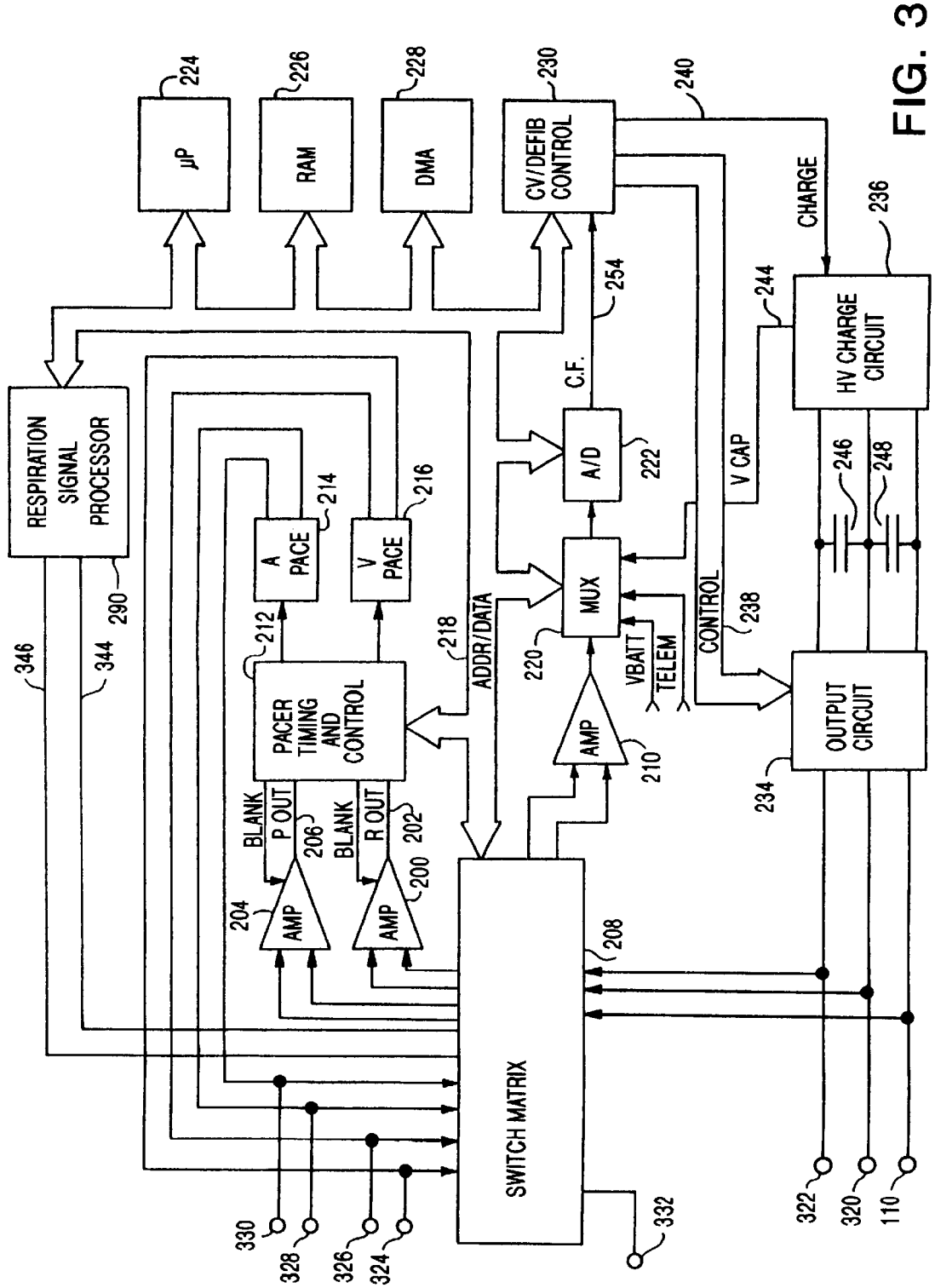
FIG. 3 is a system block diagram of the components of a comprehensive ICD or PCD IPG of the type in which the embodiments and variations of present invention may be advantageously selectively employed or combined.

The preferred embodiments of the invention are preferably implemented in the context of an implantable PCD having single or dual chamber pacing and/or cardioversion/defibrillation capabilities of the types described in detail in the above-referenced '441 patent and in commonly assigned, U.S. Pat. No. 5,549,642, respectively, incorporated herein by reference in their entireties. Such PCDs may be constructed or made programmable to provide atrial only, ventricular only, or both atrial and ventricular pacing modes. The pacing modes also preferably include either or both bradycardia compensating pacing modes or anti-tachycardia pacing therapies. In addition, the present invention may be employed with a wide variety of cardioversion electrode combinations for atrial or ventricular cardioversion FIGS. 2 and 3 illustrate a dual chamber, multi-programmable, PCD IPG 100 and associated lead system for providing atrial and ventricular sensing functions for detecting P-waves of atrial depolarizations and R-waves of ventricular depolarizations, depending on the programmed pacing and/or sensing mode and providing atrial or ventricular cardioversion therapies. An exemplary cardioversion lead system and electrodes are depicted in FIG. 2 for delivering atrial cardioversion/defibrillation shock or other therapies to the atria 12 or the ventricles 16 of the heart 10. The heart 10 is illustrated in relation to the right and left lungs 70 and 72 and the diaphragm 74. The lead system also includes impedance sensing lead 160 having at least one electrode 166 at the distal end of the lead 160 positioned across the patient's chest from the location of the IPG 100 and having a connector 162 inserted in connector block 120. The electrode 166 and the IPG can electrode 110 may be used to derive a respiration signal from impedance changes in the current pathway between them that varies with the expansion and contraction of the lungs 70, 72 and chest attendant to inspiration and expiration of air into and from lungs 70 and 72. The IPG can electrode 110 and any one of the illustrated cardioversion electrodes may alternatively be used to derive the respiration signal. FIGS. 2 and 3 are intended to provide a comprehensive illustration of each of the components sufficient to operate in accordance with each of the embodiments and variations of the invention in relation to the patients cardiovascular and respiratory system in configurations that may be effected using sub-combinations of the components depicted therein and equivalents thereto.

In the preferred embodiment of FIGS. 2 and 3, depending on the programmed pacing mode, pacing pulses may be applied to the atrium and/or ventricle in response to the detection of the appropriate bradycardia condition by the PCD IPG 100. The pacing and sensing functions are effected through atrial and ventricular bipolar pace/sense electrode pairs at the ends of right atrial/superior vena cava (RA/SVC) and right ventricular (RV) leads 140 and 116, respectively, fixed in the right atrium 12 and right ventricle 16, respectively, that are electrically coupled to the circuitry of IPG 100 through a connector block 120. The coronary sinus (CS) lead 130 includes an elongated insulating lead body enclosing one elongated coiled wire conductor coupled to an elongated exposed coil wire CS cardioversion electrode 134. CS cardioversion electrode 134, illustrated in broken outline, is located within the coronary sinus and great vein 58 of the heart 10 and may be about 5 cm in length. At the proximal end of the CS lead 130 is a connector end 132 having an exposed connector coupled to the coiled wire conductor and attached within the connector block 120 to connector block terminals in a manner well known in the art.

The RA/SVC lead 140 includes an elongated insulating lead body carrying at least three concentric, electrically isolated, coiled wire conductors separated from one another by tubular insulating sheaths. The lead body is formed in a manner well known in the art in an atrial J-shape in order to position its distal end in the right atrial appendage. An atrial pace/sense ring electrode 144 and an extendable helical, pace/sense electrode 146, mounted retractably within an insulating electrode head 148, are formed distally to the bend of the J-shape. Helical electrode 146 is adapted to be extended out of the electrode head 148 and screwed into the atrial appendage in a manner well known in the art. RA pace/sense electrodes 144 and 146 are employed for atrial pacing and for near-field sensing of P-waves. An elongated, exposed coil, RA/SVC cardioversion electrode 150 is supported on RA lead 140 extending proximally to pace/sense ring electrode 144 and coupled to the third coiled wire conductor within the RA lead body. RA/SVC cardioversion electrode 150 preferably is 10 cm in length or greater and is configured to extend from within the SVC and toward the tricuspid valve 36. At the proximal end of the RA lead 140 is a bifurcated connector 142 which carries three exposed electrical connectors, each coupled to one of the coiled wire conductors, that are attached within the connector block 120 to connector block terminals in a manner well known in the art.

The delivery of atrial cardioversion/defibrillation therapies to the atria 12 may be effected through selected combinations of intracardiac electrodes, e.g. the illustrated exemplary RA/SVC cardioversion electrode 150 and the CS cardioversion electrode 134. The exposed surface of the outer housing or can of the IPG 100 is optionally used as can electrode 110 serving as a subcutaneous remote cardioversion electrode in combination with one or more intracardiac cardioversion electrode for cardioverting or defibrillating the atria. A remote, subcutaneous defibrillation patch electrode or epicardial patch electrode may be provided in addition to or substitution for the can electrode 110.

The RV lead 116 is depicted in a conventional configuration and includes an elongated insulating lead body, enclosing at least three concentric, electrically isolated, coiled wire conductors, separated from one another by tubular insulating sheaths. Located adjacent the distal end of the RV lead 116 are a pace/sense ring electrode 124, and a helical, pace/sense electrode 126, mounted retractably within an insulating electrode head 128. Helical electrode 126 is adapted to be extended out of the electrode head 128 and screwed into the ventricular apex in a manner well known in the art. RV pace/sense electrodes 124 and 126 are each coupled to a coiled wire conductor within the RV lead body and are employed for cardiac pacing in the ventricle and for sensing near-field R-waves. In the embodiments of the present invention devoted to delivering ventricular cardioversion therapies, the RV lead 116 also supports an elongated, exposed wire coil, cardioversion electrode 170 in a distal segment thereof adapted to be placed in the right ventricle 16 of heart 10 and connected to a further coiled wire conductor within the RV lead body. Although not specifically illustrated in FIG. 2, it will be understood that the ventricular cardioversion therapies may be delivered between further RV cardioversion electrode in combination with the intracardiac RV cardioversion electrode 170 or between the intracardiac ventricular cardioversion electrode and the IPG can electrode 110 and/or the CS cardioversion electrode 134 or the RA/SVC cardioversion electrode 150. At the proximal end of the RV lead 116 is a bifurcated connector end 118 having a plurality of electrical connectors, each coupled to one of the coiled conductors in the RV lead body, that are attached within the connector block 120 to connector block terminals in a manner well known in the art Certain embodiments of the present invention work more efficaciously with cardioversion electrodes substantially in contact with the heart chambers. Atrial or ventricular epicardial cardioversion electrodes may be used instead of one or more of the illustrated intracardiac cardioversion electrodes of FIG. 2 if they are flexible and do not interfere with the deflation or compression of the heart chamber. When the heart chambers are deflated on blood emptying or subjected to compression at end inspiration, the total impedance between the electrode pairs decreases. However, when one or more remote, subcutaneous patch or can electrode is employed, the total impedance between the electrode pairs may increase at the end inspiration point or phase due to the expansion of the chest and inflation of the lungs, increasing the distance between the cardioversion electrode pair. In this case, the optimum respiration point or phase for delivery of the cardioversion therapy may be the end of expiration or the beginning of ispiration. Delivery of cardioversion/defibrillation therapy may be synchronized to the patient's normal respiratory cycle or the patient may optionally extend the end expiration point by holding his/her breath.

FIG. 3 is a functional schematic diagram of the circuitry of a dual chamber, implantable PCD IPG 100 in which the present invention may usefully be practiced. Certain of the pace/sense and cardioversion/defibrillation functions and associated leads and electrodes may be disabled or not provided to configure the PCD system to operate in accordance with the preferred embodiments and variations described below. In all such embodiments and variations, the atrial pacing capability may be eliminated. Therefore, FIG. 3 should be taken as exemplary of the circuitry of the type of single chamber or dual chamber PCD IPG 100 in which the invention may be embodied, and not as limiting, as it is believed that the invention may usefully be practiced in a wide variety of device implementations, as long as a pacing mode providing either bradycardia pacing or tachycardia pacing therapies is retained.

The PCD IPG circuitry of FIG. 3 includes a high voltage section for providing relatively high voltage cardioversion/defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided in a manner well known in the art.

The block diagram of FIG. 3 depicts the atrial and ventricular pace/sense lead connector terminals 328, 330 and 326, 324, respectively, the atrial and ventricular cardioversion/defibrillation lead connector terminals 322, 320, and the impedance lead 160 connector terminal 332, all within the connector block 120, and a hard wired connection with the can electrode 110.

A respiration signal detection mode is also initiated by microprocessor 224 when the tachyarrhythmia is initially detected at onset or is confirmed in order to time the delivery of the cardioversion therapy to the heart chamber. The switch network 208 is selectively operated by the microprocessor 224 to couple the can electrode 110 through conductor 344 to one input/output terminal of impedance signal processor 290 and to couple a further electrode selected from among the electrodes in the lead system in use through conductor 346 to the other input/output terminal of impedance signal processor 290. In the example depicted in FIG. 2, the separate impedance lead 160 and impedance electrode is provided in the lead system and is attached to terminal 332 in the block diagram of FIG. 3, However, another electrode could be selected in switch matrix 208, eliminating the need for the impedance lead 160.

Assuming the use of the separate impedance lead 160, when the impedance signal processor 290 is enabled by the microprocessor 224, it supplies a low energy, constant current signal to the spaced apart respiration electrodes 166 and 110 through the conductors 344 and 346 and enabled switches in switch network 208. The voltage across the input/output terminals of the impedance signal processor 290 changes as a function of the change in impedance of the current pathway across the patient's chest between the impedance electrode 166 and can electrode 110. The impedance change is a function of the change in distance in the current pathway within the chest and across the lungs 70, 72 and between the selected impedance electrodes 110 and 166 which increases with inspiration and decreases with expiration.

Such impedance signal deriving and processing techniques for use in the present invention are known in the prior art employed in other applications. For example, impedance plethysmography using separate impedance electrodes or pace/sense electrodes to derive a physiologic signal related to patient exercise that is processed to determine an optimum bradycardia pacing rate is disclosed in U.S. Pat. Nos. 4,702,253 and 4,697,591, incorporated herein by reference. An extensive discussion of prior art impedance measuring systems, electrodes, and techniques for a variety of medical device uses is set forth in U.S. Pat. No. 5,179,946, incorporated herein by reference. In the '946 patent and U.S. Pat. No. 5,385,576, the cardiac impedance including the blood impedance in the heart chambers is used to determine or classify tachyarrhythmias that result in hemodynamic compromise, and the fluctuations of the impedance signal due to respiration are ignored or filtered out.

By contrast, in the present invention, the magnitude and frequency of the change of the impedance signal corresponding to the tidal volume and the respiration rate are employed to determine the optimum reduction in interelectrode impedance in the path between the particular set of cardioversion electrodes. The minor fluctuations in the impedance signal due to cardiac function are ignored. The measurement of the change in impedance as reflected by an increase in the voltage signal can be used as one method for determining when inspiration begins and reaches end, inspiration in the respiratory cycle. As inspiration begins, the chest swells, decreasing the size of the pleural cavity and compressing the atria 12. At the same time, the respiration cycle has an influence on the autonomic nerves as shown in FIG. 1. The sympathetic nerve activity increasing during inspiration may lead to increased excitability of atrial cells and lower the energy required to cardiovert the atria. Moreover, it is postulated in accordance with the invention that the increase in pleural impedance may also act to insulate the heart so that the atrial or ventricular cardioversion energy delivered directly to the heart through intracardiac and/or epicardial electrodes is concentrated within the atria or ventricles, respectively.

In one form of practicing the second embodiment of the invention, the physician can test the efficacy of the respiration detection system in a patient work-up after or during the implantation of the system. Using an external programmer in a manner known in the art, the physician can initiate the operation of the respiration signal processor and telemetry out of the impedance signal levels as the patient breathes and is instruct to hold his/her breath at end inspiration and end expiration. Based on the observed impedance fluctuations, the physician may then program in respiration threshold signal levels to be maintained in RAM 226 as programmed values to be used in comparison with the measured impedance signal levels as described below. A self learning or adaptive program may alternatively be used to establish the threshold levels or otherwise directly determine the end inspiration and end expiration point or phase.

Returning to FIG. 3 and assuming that the system is configured to respond to atrial tachyarrhythmias and to deliver cardioversion therapies to the atria, terminal 322 is adapted to be coupled through RA lead 140 to RA/SVC electrode 150 and terminal 320 is adapted to be coupled through CS lead 130 to CS cardioversion electrode 134. Terminals 322, 320 and, alternatively, can electrode 110 are coupled to high voltage (HV) output circuit 234 which includes high voltage switches controlled by CV/DEFIB CONTROL logic 230 via control bus 238. The switches within HV output circuit 234 control which cardioversion electrodes are employed and which are coupled to the positive and negative terminals of the capacitor bank including capacitors 246 and 248 during delivery of intermediate and high voltage cardioversion and defibrillation shocks.

Terminals 324 and 326 of the connector block are adapted to be coupled through RV lead 116 to RV pace/sense electrodes 124 and 126 for sensing and pacing in the ventricle. Terminals 328 and 330 are adapted to be coupled through RA/SVC lead 140 to RA pace/sense electrodes 144 and 146 for sensing and pacing in the atrium. Terminals 324 and 326 are coupled to the inputs of Ventricular sense amplifier 200 through switches in switch network 208. Ventricular sense amplifier 200 which preferably takes the form of an automatic gain controlled amplifier providing an adjustable sensing threshold as a function of the measured R-wave signal amplitude. A VSENSE signal is generated on R-OUT line 202 whenever the signal sensed between electrodes 124 and 126 exceeds the current ventricular sensing threshold. Terminals 328 and 330 are coupled to the atrial sense amplifier 204 through switches in switch network 208. Atrial sense amplifier 204 preferably also takes the form of an automatic gain controlled amplifier providing an adjustable sensing threshold as a function of the measured P-wave amplitude. An ASENSE signal is generated on P-OUT line 206 whenever the signal sensed between pace/sense electrodes coupled to terminals 328, 330 exceeds the current atrial sensing threshold. The A-PACE and V-PACE output circuits 214 and 216 are also coupled to terminals 328, 330 and 324, 326, respectively. The atrial and ventricular sense amplifiers 204 and 200 are isolated from the A-PACE and V-PACE output circuits 214 and 216 by appropriate isolation switches within switch matrix 208 and also by blanking circuitry operated by A-BLANK and V-BLANK signals during and for a short time following delivery of a pacing pulse in a manner well known in the art. The general operation of the ventricular and atrial sense amplifiers 200 and 204 may correspond to that disclosed in U.S. Pat. No. 5,117,824, incorporated herein by reference in its entirety.

Switch matrix 208 is also used in an EGM sensing mode to select which of the available pace/sense electrodes (or cardioversion electrodes) are coupled to the inputs of wide band (0.5–200 Hz) EGM sense amplifier 210 for use in digital signal storage and analysis of the patient's atrial and ventricular EGM. Therefore, the terminals 328, 330, adapted to be coupled to the atrial pace/sense electrodes 144, 146, and the terminals 324, 326, adapted to be coupled to the ventricular pace/sense electrodes 124, 126, are also coupled to the switch matrix 208. Switches within switch matrix 208 are selectively controlled by the microprocessor 224 or circuits within the pacer timing and control circuitry 212, via data/address bus 218, to couple the terminals 328, 330 or 324, 326 to the inputs of band pass amplifier 210 and to thereby apply atrial or ventricular signals to the band pass amplifier 210. Output signals from band pass amplifier 210, in response to the applied atrial or ventricular signals, are provided to multiplexer 220, and thereafter converted to multi-bit digital signals by A/D converter 222, for storage in RAM in ROM/RAM 226 under control of DMA 228. Microprocessor 224 may employ digital signal and morphology analysis techniques to characterize the digitized signals stored in ROM/RAM 226 to recognize and classify the patient's heart rhythm employing any of the numerous signal processing methodologies known to the art.

The PCD IPG circuitry of FIG. 3 provides atrial and/or ventricular cardiac pacing for bradycardia and tachycardia conditions and atrial synchronized cardioversion/defibrillation therapies atrial fibrillation/flutter in accordance with the timing algorithms described below and therapy regimes programmed by the physician. With respect to the pacing operations, the pacer timing and control circuitry 212 includes programmable digital counters which control the basic time intervals associated with bradycardia pacing modes including DDD, VVI, DVI, VDD, AAI, DDI and other modes of single and dual chamber pacing well known to the art. Pacer timing and control circuitry 212 also controls escape intervals associated with timing and delivering anti-tachyarrhythmia pacing in both the atrium and the ventricle, employing any anti-tachyarrhythmia pacing therapies known to the art. In the process, pacer timing and control circuitry 212 also times the operation of and processes ASENSE and VSENSE events on the P-OUT and R-OUT lines of the atrial and ventricular sense amplifiers 204 and 200.

In normal pacing modes of operation, intervals defined by pacer timing and control circuitry 212 include atrial and ventricular pacing escape intervals, blanking intervals, refractory periods and pulse widths of pacing pulses. These intervals are determined by microprocessor 224, in response to stored data in RAM in ROM/RAM 226 and are communicated to the pacer timing and control circuitry 212 via address/data bus 218. Pacer timing and control circuitry 212 also determines the amplitude of the cardiac pacing pulses under control of microprocessor 224.

During pacing, the atrial and ventricular escape interval counters within pacer timing and control circuitry 212 are reset upon non-refractory ASENSE and VSENSE events on lines 202 and 206. In accordance with the selected pacing mode, pacer timing and control circuitry 212 provides pace trigger signals to the A-PACE and V-PACE output circuits 214 and 216 on time-out of the appropriate escape interval counters to trigger generation of atrial and/or ventricular pacing pulses. The pacing escape interval counters are also reset on generation of pacing pulses, and thereby control the basic timing of cardiac pacing functions.

Microprocessor 224 operates as an interrupt driven device responsive to interrupts from pacer timing and control circuitry 212 corresponding to the ASENSE and VSENSE events and provided via data/address bus 218. Any necessary mathematical calculations to be performed by microprocessor 224 and any updating of the values or intervals controlled by pacer timing/control circuitry 212 take place following such interrupts.

For example, in response to a VSENSE, the V-V interval separating that VSENSE from the most recent VSENSE or V-PACE or the P-R interval separating that VSENSE from an immediately preceding ASENSE or P-PACE may be stored temporarily in memory. Similarly, in response to an ASENSE, the A-A interval separating that ASENSE from the most recent preceding ASENSE or A-PACE or the V-A interval separating that ASENSE from the immediately preceding VSENSE or R-PACE may be stored temporarily in memory. Preferably, a portion of RAM in the ROM/RAM 226 (FIG. 3) is configured as a plurality of recirculating buffers, capable of holding a preceding series of such measured intervals, which may be analyzed to determine whether the patient's heart is presently exhibiting atrial or ventricular tachyarrhythmia, and, in the context of the atrial system, whether a ventricular rhythm is present and regular enough to be employed in timing the delivery of the atrial cardioversion therapy as described below.

In the atrial cardioversion context, pacer timing and control circuitry 212 determines the presence of a high rate atrial (or ventricular) tachycardia or atrial fibrillation/flutter from timing and regularity of the stored A-A intervals in a manner well known in the art. For example, presence of atrial tachyarrhythmia may be confirmed by means of detection of a sustained series of short A-A intervals of an average rate indicative of tachyarrhythmia or an unbroken series of a certain number of successive short A-A intervals. The suddenness of onset of the detected high rate, the stability of the high rate, or a number of other factors known to the art may also be measured at this time. The comparative V-V intervals as well as the absence or diminution of the atrial ICBP wave fluctuation in synchrony with ASENSE events may also be employed in confirming the presence of the atrial tachyarrhythmia.

In the event that an atrial tachyarrhythmia is detected and confirmed, and an initial anti-tachyarrhythmia pacing regimen is prescribed, appropriate timing intervals for controlling generation of anti-tachyarrhythmia pacing therapies are loaded from microprocessor 224 into the pacer timing and control circuitry 212. The timed or burst pacing therapies are delivered by the A-PACE pulse generator 214 to the atrial pace/sense electrodes in a manner well known in the art. In accordance with one aspect of the present invention, the timing of delivery of such anti-tachyarrhythmia pacing therapies may also be governed by the algorithms described below in the context of delivering a cardioversion shock therapy.

In response to the detection of atrial (or ventricular) fibrillation or tachyarrhythmia requiring a cardioversion shock therapy, microprocessor 224 activates cardioversion/ defibrillation control circuitry 230, which initiates charging of the high voltage capacitors 246 and 248 via charging circuit 236, under control of high voltage charging control line 240. The voltage on the high voltage capacitors is monitored via VCAP line 244, and the monitored voltage signal is passed through multiplexer 220, digitized, and compared to a predetermined value set by microprocessor 224 in ADC/comparator 222. When the voltage comparison is satisfied, a logic signal on Cap Full (CF) line 254 is applied to cardioversion/defibrillation control circuit 230, terminating charging. Thereafter, timing of the delivery of the defibrillation or cardioversion shock is controlled by pacer timing/control circuitry 212 using the timing criteria described below for timing the delivery to a programmed point or phase of the respiratory cycle. Following delivery of the cardioversion shock therapy, the microprocessor 224 then returns the operating mode to cardiac pacing and awaits the next successive interrupt due to pacing or the occurrence of a sensed atrial or ventricular depolarization.

In the illustrated IPG circuit of FIG. 3, delivery of the cardioversion shocks is accomplished by output circuit 234, under control of control circuitry 230 via control bus 238. Output circuit 234 determines whether a monophasic or biphasic shock is delivered, the polarity of the cardioversion electrodes and which cardioversion electrodes are involved in delivery of the shock or shocks. Output circuit 234 also includes high voltage switches which control whether cardioversion electrodes are coupled together during delivery of the shock. Alternatively, cardioversion electrodes intended to be coupled together during the shock may simply be permanently coupled to one another, either exterior to or interior of the device housing, and polarity may similarly be pre-set, as in current ICDs and PCDs. An example of output circuitry for delivery of biphasic shock regimens to multiple electrode systems may be found in U.S. Pat. No. 4,727,877, incorporated by reference in its entirety.

The particular cardioversion therapies are programmed in during a patient work up by the physician, and a menu of therapies is typically provided. For example, on initial detection of an atrial (or ventricular) tachycardia, an antitachycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial fibrillation is identified, the typical therapy will be delivery of a high amplitude cardioversion shock, typically up to 4.0 Joules. It is envisioned that the amplitude of the cardioversion shock may be incremented in response to failure of an initial shock energy to terminate the tachyarrhythmia.

A number of embodiments and variations of algorithms for implementing the timing of the delivery of the atrial cardioversion therapies are set forth in the following discussion. It will be understood that these algorithms may be implemented in the PCD IPG as one or more of a series of therapies that may be delivered in a programmable regimen in response to a tachyarrhythmia episode. Further, more aggressive, therapies may be invoked upon failure of a given therapy to achieve cardioversion.

Figure 4:
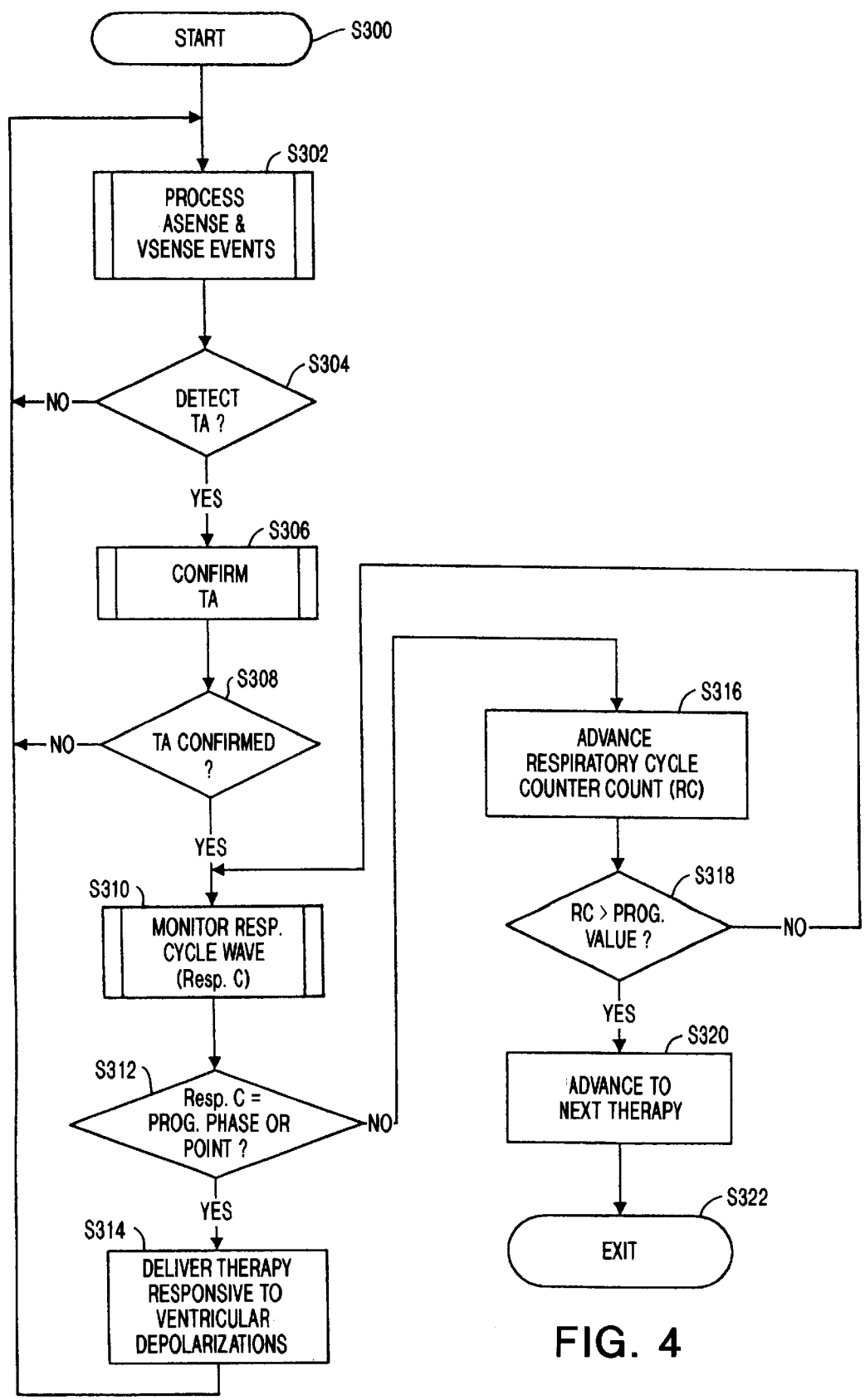
FIG. 4 is a flow chart of the operation of selected components of the system of FIGS. 2 and 3 in a an operating mode timing delivery of the cardioversion therapy to a programmed phase of the respiratory cycle dependent upon the types of cardioversion electrodes employed in the system.
Figure 5:
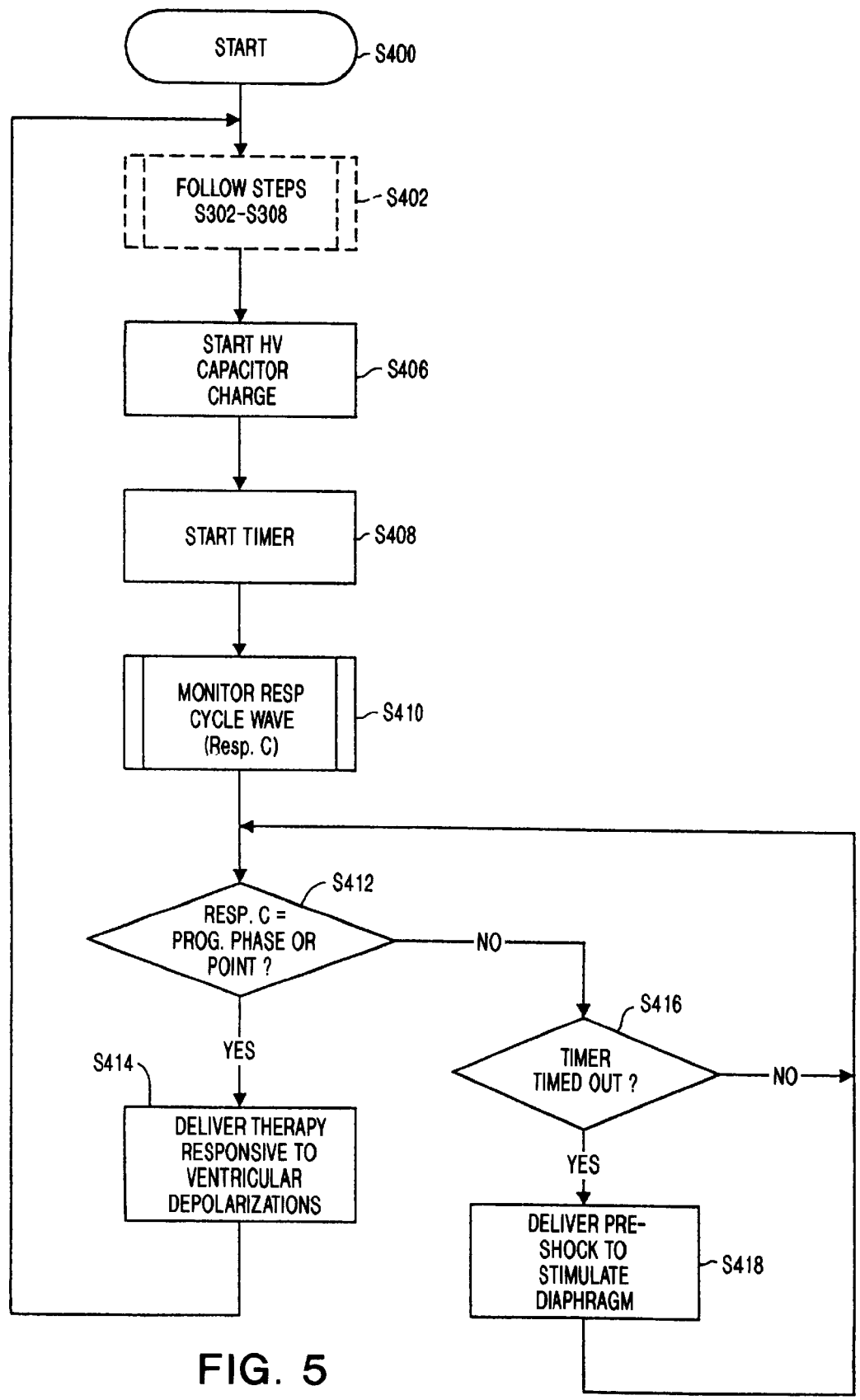
FIG. 5 is a further flow chart of the operation of selected components of the system of FIGS. 2 and 3 in a variation of the operating mode illustrated in FIG. 4 providing a pre-shock of the diaphragm to stimulate a respiratory cycle.

FIG. 4 is a flow chart of the operation of the system of FIGS. 2 and 3 in a first operating mode timing delivery of the cardioversion therapy to a programmed phase of the respiratory cycle. In the context of treating atrial tachyarrhythmias the delivery of the atrial cardioversion therapy to the programmed phase of the respiratory cycle is in recognition that the atrial volume and the autonomic tone for sustenance of atrial fibrillation/flutter are influenced by the respiratory cycle as described above with reference to FIG. 1.

In step S302, the ASENSE and VSENSE events and other parameters are monitored and processed from which the existence of a tachyarrhythmia (TA) can be determined. In steps S304–S308, the presence of a tachyarrhythmia of the types described above for the particular heart chamber being monitored and treated is detected and confirmed employing the above-described conventional methods. If the programmed therapy constitutes a cardioversion shock therapy, charging of the high voltage output capacitors is commenced at this point as described above in reference to FIG. 3.

The fluctuation of the respiratory cycle is preferably determined in step S310 by enabling the impedance signal processor 290 and the switch network 208 to couple the selected impedance sensing electrodes to it. The start and end of the inspiration and expiration phases or other selected attributes of the respiration cycle are determined in step S310 from the impedance (voltage) signal amplitude or rate of change or other measured parameter. As explained above, the optimum point or phase of the respiratory cycle may be the end of inspiration or the end of expiration/beginning of inspiration, depending on the selection of cardioversion electrodes implanted in the or around the patient's heart, and is programmed into the IPG memory as either the maximum or minimum impedance (voltage) signal level. At step S310, the impedance (voltage) waveform is sampled, and sample values are successively compared to one another over the respiratory cycle by the respiration signal processor 290 to determine the minimum or maximum signal level. A succession of maximum or minimum sample values may be used to determine the programmed inspiration or respiration phase, respectively. The programmed point is achieved when the maximum or minimum respiration signal amplitude is determined, and the programmed phase may constitute an indefinite continuation of the point due to a voluntary holding of the breath or absence of breathing. As described above, the programmed optimum phase or point to realize the lowest energy cardioversion shock level or the most efficacious cardioversion therapy is selectable by the physician in relation to the types of cardioversion electrodes implanted in the patient's body and dependent on the results of a patient work-up. When the programmed phase or point is determined in step S312, the delivery of the cardioversion therapy is initiated in step S314.

In the case where the cardioversion therapy is a cardioversion shock, it may take several seconds for the high voltage output capacitors to charge to the programmed voltage. The monitoring of the respiratory cycle commences in step S310 during the charging time, but determination of the programmed phase or point of the respiratory cycle in step S310 is delayed until confirmation is received on C. F. line 254.

Once the programmed point or phase of the respiratory cycle is determined, the delivery of the cardioversion therapy is preferably timed to a certain programmable feature of the monitored cardiac signal. To do so, step S314 also preferably includes a ventricular synchronization process. Delivery of atrial cardioversion/defibrillation shocks should be timed relative to sensed or paced ventricular depolarizations such that the cardioversion/defibrillation pulses fall outside the ventricular vulnerable period, either by delivery of the cardioversion pulses synchronized closely to the ventricular depolarization as in U.S. Pat. No. 5,584,868, issued to White, incorporated herein by reference in its entirety or following a delay period initiated on the ventricular depolarization as in U.S. Pat. No. 5,211,524, issued to Mehra, also incorporated herein by reference in its entirety. Ventricular cardioversion/cdefibrillation pulses may be syncronized to ventricular depolarizations as disclosed in U.S. Pat. No. 5,188,105, issued to Keimel or U.S. Pat. No. 5,275,621, issued to Mehra, both incorporated herein by refrence in their entireties. After delivery of the cardioversion therapy in step S314, the algorithm loops back to step S302 to determine if the therapy has succeeded.

Steps S300–S314 represent the simplest implementation of the preferred embodiment in respect to timing the delivery of cardioversion therapies to an appropriate phase or point of the respiration cycle. In the simplest implementation, if the programmed phase or point of the respiratory cycle cannot be determined, then the attempt to synchronize delivery of the cardioversion therapy to the respiratory cycle may be abandoned. To do so, a therapy timer may be started when the cardioversion therapy is ready to be delivered (e.g. when the high voltage output capacitors are fully charged) during which time steps S310 and S312 must be realized.

In a further variation of the simplest implementation, it will be assumed that the determination made in step S312 involves a comparison of the measured and sampled respiration impedance signal to programmed threshold minimum or maximum values. If, as a result of the comparison, the programmed point or phase cannot be determined in step S312 in a first respiration cycle, then a respiration cycle counter count (RC) is incremented in step S316. The incremented RC is compared to a programmed count value in step S318, and if a number of respiratory cycles are completed without a successful determination of the programmed point or phase, then the back-up cardioversion therapy is delivered in step S320. The back-up therapy in this case may constitute abandoning the attempt to synchronize the delivery of the cardioversion therapy to the respiration cycle and resorting directly to attempting to synchronize the delivery to the VSENSE event after the ventricular safety delay in step S314.

Turning to FIG. 4, it illustrates a further variation of the preferred embodiment of the invention that may be incorporated with any of the above described variations particularly for use when a cardioversion shock therapy is to be delivered and wherein step S402 follows steps S302–S308 as described above. The charging of the high voltage output capacitors is commenced in step S406, and a therapy timer is started in step S408 either during charging or following the achievement of full charge. In the event that the programmed phase or point cannot be determined in step S410 before the therapy timer times out, it is assumed that the patient is breathing too shallowly for measurement purposes or not at all. In this case, a low energy pre-shock is delivered between the cardioversion electrodes in step S418 which is intended to stimulate the diaphragm into forcefully contracting. If the pre-shock is successful, the contraction occurs immediately, and the programmed phase of the cardiac cycle can the be determined in step S312. The energy level of the pre-shock sufficient to elicit a respiration cycle from which the programmed phase or point may be determined may also be programmed by the physician in a patient work-up.

It will be understood that in each such embodiment, staged therapies of increasing energy level may be provided by programming of the IPG operating mode. If the applied therapy is not successful, then a higher energy therapy may be provided. In commercial implementations, the invention may be embodied as part of an implantable PCD system, particularly for providing cardioversion therapies, of the types disclosed in commonly assigned U.S. Pat. Nos. 5,165,403, 5,292,338 or 5,314,430 employing two or more cardioversion electrodes arrayed in operative relation to the chamber of the heart. Alternatively, the present invention may be employed as part of an implantable arrhythmia control device including or substituting other cardioversion therapies of the types described above in pre-treatment of the chamber or substitution for the cardioversion shock therapy. The present invention is directed to the timing of the delivery of such cardioversion therapies, rather than the type of therapy, such that it is delivered when an optimum point or phase of the respiratory cycle is achieved for the particular cardioversion electrode configuration for delivering cardioversion therapies to the chamber, such that the chamber is most receptive to being converted to normal sinus rhythm.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

In conjunction with the above disclosure, we claim:

1. A method of effecting atrial cardioversion, comprising:
    implanting cardioversion electrodes in a patient's body;
    monitoring the patient's cardiac cycle;
    detecting an atrial tachyarrhythmia from the monitored cardiac cycle;
    monitoring the patient's respiratory cycle;
    detecting an optimum point or phase of the respiratory cycle affecting the volume of the patient's lungs and the impedance between the cardioversion electrodes;
    defining acceptable times for delivery of cardioversion therapy relative to ventricular depolarizations;
    detecting occurrences of ventricular depolarizations; and
    delivering the cardioversion therapy at an acceptable time relative to ventricular depolarizations within the determined optimum point or phase of the respiratory cycle.

2. The method of claim 1 wherein the step of detecting a point or phase of the respiratory cycle further comprises detecting the end of expiration or the beginning of inspiration.

3. The method of claim 2 wherein the implanting step comprises implanting at least one of the cardioversion electrodes in the patient's body remotely from the patient's atria.

4. The method of claim 1 further comprising the step of delivering a cardioversion therapy to the patient's atria in response to a failure to detect said optimum point or phase of the respiratory cycle.

5. A method of effecting atrial cardioversion between cardioversion electrodes substantially in contact with a patient's atria at a minimal energy comprising the steps of:
    monitoring the cardiac cycle;

detecting an atrial tachyarrhythmia from the monitored cardiac cycle;

monitoring the respiratory cycle of the patient;

detecting a point or phase of the respiratory cycle during which atrial volume is minimized; and delivering a cardioversion therapy across the cardioversion electrodes in contact with the atria timed to substantially coincide with the detected point or phase of the respiratory cycle.

6. The method of claim 5 wherein the delivering step further comprising the steps of:

defining acceptable times for delivery of the cardioversion therapy relative to ventricular depolarizations;

detecting occurrences of ventricular depolarizations; and delivering the cardioversion therapy at an acceptable time relative to ventricular depolarizations within the determined optimum point or phase of the respiratory cycle.

7. The method of claim 5 wherein the step of detecting a point or phase of the respiratory cycle further comprises detecting the end of inspiration.

8. A method of effecting cardioversion of a heart chamber through the application of a cardioversion shock therapy to cardioversion electrodes implanted in a patient's body comprising the steps of:

monitoring the patient's cardiac cycle;

detecting a tachyarrhythmia of the heart chamber from the monitored cardiac cycle;

monitoring the patient's respiratory cycle;

timing a therapy time interval for monitoring of the respiratory cycle following detection of the tachyarrhythmia;

determining an optimum point or phase of the respiratory cycle affecting the volume of the patient's lungs and the impedance between the cardioversion electrodes within the therapy time interval;

delivering a cardioversion therapy to the cardioversion electrodes timed to substantially fall within the determined optimum point or phase of the respiratory cycle during the therapy time interval; and delivering a cardioversion therapy to the patient's heart chamber in response to a failure to detect said optimum point or phase of the respiratory cycle.

9. Apparatus for effecting atrial cardioversion through the application of a cardioversion therapy to cardioversion electrodes implanted in a patient's body comprising:

means for defining an optimal point or phase of the patients respiratory cycle;

means for monitoring the patient's cardiac cycle;

means for detecting an atrial tachyarrhythmia from the monitored cardiac cycle;

means for monitoring the patient's respiratory cycle;

means for detecting the optimum point or phase of the respiratory cycle;

means for detecting ventricular depolarizations;

means for defining acceptable times for delivery of the cardioversion therapy relative to ventricular depolarizations; and means for delivering the cardioversion therapy at an acceptable time relative to ventricular depolarizations within the detected optimum point or phase of the respiratory cycle.

10. The apparatus of claim 9 wherein the means of detecting a point or phase of the respiratory cycle further comprises means for detecting the end of expiration or beginning of inspiration.

11. The apparatus of claim 10 wherein at least one of the cardioversion electrodes is adapted to be implanted in the patient's body remotely from the patient's atria.

12. The apparatus of claim 9 wherein the delivering means further comprises means for providing a cardioversion therapy to the patient's atria in response to a failure to detect said optimum point or phase of the respiratory cycle.

13. A method of effecting cardioversion of a heart chamber, comprising:

implanting cardioversion electrodes in a patient's body;

monitoring the patient's cardiac cycle;

detecting a tacharrhythmia of the heart chamber from the monitored cardiac cycle;

monitoring the patient's respiratory cycle;

detecting an optimum point or phase of the respiratory cycle affecting the volume of the patient's lungs and the impedance between the cardioversion electrodes; and delivering a cardioversion therapy to the cardioversion electrodes timed to substantially fall within the detected optimum point or phase of the respiratory cycle; and wherein the step of detecting a point or phase of the respiratory cycle comprises detecting the end of inspiration.

14. The method of claim 13 wherein the implanting step comprises implanting the cardioversion electrodes in contact with the heart chamber.

15. The method of claim 13 further comprising the step of delivering a cardioversion therapy to the heart chamber in response to a failure to detect said optimum point or phase of the respiratory cycle.

16. A method of effecting cardioversion of a heart chamber through the application of a cardioversion shock therapy to cardioversion electrodes implanted in a patient's body comprising the steps of:

monitoring the patient's cardiac cycle;

detecting a tachyarrhythmia of the heart chamber from the monitored cardiac cycle;

monitoring the patient's respiratory cycle;

timing a therapy time interval for monitoring of the respiratory cycle following detection of the tachyarrhythmia;

determining an optimum point or phase of the respiratory cycle affecting the volume of the patient's lungs and the impedance between the cardioversion electrodes within the therapy time interval;

delivering a cardioversion therapy to the cardioversion electrodes timed to substantially fall within the determined optimum point or phase of the respiratory cycle during the therapy time interval; and providing a pre-shock to a cardioversion electrode in response to a failure to detect said optimum point or phase of the respiratory cycle within the therapy time interval for eliciting a respiration cycle through a stimulated contraction of the diaphragm.

17. Apparatus for effecting atrial cardioversion through the application of a cardioversion therapy to cardioversion electrodes implanted in a patient's body comprising:

means for defining an optimal point or phase of the patients respiratory cycle;

means for monitoring the patient's cardiac cycle;

means for detecting an atrial tachyarrhythmia from the monitored cardiac cycle;

means for monitoring patient's respiratory cycle;

means for detecting the optimum point or phase of the respiratory cycle; and means for delivering a cardioversion therapy to the cardioversion electrodes timed to substantially fall within the detected optimum point or phase of the respiratory cycle; and wherein the means of detecting a point or phase of the respiratory cycle comprises means for detecting the end of inspiration.

18. The apparatus of claim 17 wherein the cardioversion electrodes are adapted to be implanted substantially in contact with the heart chamber.

19. The apparatus of claim 17 wherein the delivering means further comprises means for providing a cardioversion therapy to the heart chamber in response to a failure to detect said optimum point or phase of the respiratory cycle.

20. Apparatus for effecting atrial cardioversion between cardioversion electrodes substantially in contact with a patient's atria at a minimal energy comprising:

means for defining an optimal point or phase of the patient's respiratory cycle;

means for monitoring the patient's cardiac cycle;

means for detecting an atrial tachyarrhythmia from the monitored cardiac cycle;

means for monitoring the respiratory cycle of the patient;

means for detecting a point or phase of the respiratory cycle;

means for delivering a cardioversion therapy across the cardioversion electrodes in contact with the atria timed to substantially coincide with the detected point or phase of the respiratory cycle; and wherein the means of detecting a point or phase of the respiratory cycle further comprises means for determining the end of inspiration.

21. The apparatus of claim 20 wherein the delivery means of comprises means for providing a back-up cardioversion therapy to the patient's heart chamber in response to a failure to determine said optimum point or phase of the respiratory cycle.

22. Apparatus for effecting cardioversion of a heart chamber through the application of a cardioversion shock therapy to cardioversion electrodes implanted in the patient's body comprising:

means for defining an optimal point or phase of the patient's respiratory cycle;

means for monitoring the patient's cardiac cycle;

means for detecting a tachyarrhythmia of the heart chamber from the monitored cardiac cycle;

means for monitoring the patient's respiratory cycle;

means for timing a therapy time interval for monitoring of the respiratory cycle following detection of the tachyarrhythmia;

means for detecting an optimum point or phase of the respiratory cycle affecting the volume of the patient's lungs and the impedance between the cardioversion electrodes within the therapy time interval; and means for delivering a cardioversion therapy to the cardioversion electrodes timed to substantially fall within the detected optimum point or phase of the respiratory cycle during the therapy time interval; and wherein the deliver means for further comprises means for providing a back-up cardioversion therapy to the patient's heart chamber in response to a failure to determine said optimum point or phase of the respiratory cycle within the therapy time interval.

23. The apparatus of claim 22 wherein the delivery means for further comprises means for providing a back-up cardioversion therapy to the patient's heart chamber in response to a failure to determine said optimum point or phase of the respiratory cycle within the therapy time interval.

24. Apparatus for effecting cardioversion of a heart chamber through the application of a cardioversion shock therapy to cardioversion electrodes implanted in the patient's body comprising:

means for defining an optimal point or phase of the patient's respiratory cycle;

means for monitoring the patient's cardiac cycle;

means for detecting a tachyarrhythmia of the heart chamber from the monitored cardiac cycle;

means for monitoring the patient's respiratory cycle;

means for timing a therapy time interval for monitoring of the respiratory cycle following detection of the tachyarrhythmia;

means for detecting an optimum point or phase of the respiratory cycle affecting the volume of the patient's lungs and the impedance between the cardioversion electrodes within the therapy time interval;

means for delivering a cardioversion therapy to the cardioversion electrodes timed to substantially fall within the detected optimum point or phase of the respiratory cycle during the therapy time interval; and means for providing a pre-shock to a cardioversion electrode in response to a failure to determine said optimum point or phase of the respiratory cycle within the therapy time interval for eliciting a respiration cycle through a stimulated contraction of the diaphragm.

* * * * *